United States Patent
Soucaille

(10) Patent No.: US 9,034,615 B2
(45) Date of Patent: May 19, 2015

(54) GLYCOLIC ACID PRODUCTION BY FERMENTATION FROM RENEWABLE RESOURCES

(75) Inventor: Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 216 days.

(21) Appl. No.: 12/302,730

(22) PCT Filed: Jun. 7, 2007

(86) PCT No.: PCT/EP2007/055625
§ 371 (c)(1),
(2), (4) Date: Nov. 26, 2008

(87) PCT Pub. No.: WO2007/141316
PCT Pub. Date: Dec. 13, 2007

(65) Prior Publication Data
US 2009/0155867 A1   Jun. 18, 2009

(30) Foreign Application Priority Data
Jun. 9, 2006 (WO) ................ PCT/EP2006/063046

(51) Int. Cl.
*C12P 7/42* (2006.01)
*C12P 7/62* (2006.01)
*A01N 63/00* (2006.01)
*C07H 3/02* (2006.01)
*C12N 15/70* (2006.01)
*C07K 14/195* (2006.01)

(52) U.S. Cl.
CPC ... *C12P 7/42* (2013.01); *C07H 3/02* (2013.01); *C12P 7/62* (2013.01); *C12N 15/70* (2013.01); *C07K 14/195* (2013.01)

(58) Field of Classification Search
CPC ............... C12P 7/42; C12P 7/62; C07H 3/02; C07K 14/195; C12N 15/70
USPC .................................. 435/135, 146; 424/93.2
See application file for complete search history.

(56) References Cited

U.S. PATENT DOCUMENTS

| | | | |
|---|---|---|---|
| 3,843,781 A * | 10/1974 | Masuda et al. | 424/76.2 |
| 3,867,440 A * | 2/1975 | Kobetz et al. | 562/579 |
| 7,445,917 B2 * | 11/2008 | DiCosimo et al. | 435/146 |
| 8,703,999 B2 * | 4/2014 | Barnicki et al. | 562/580 |
| 2008/0032370 A1 | 2/2008 | Wada et al. | |

FOREIGN PATENT DOCUMENTS

| | | |
|---|---|---|
| JP | 19950204062 | 2/1997 |
| WO | 2005/047498 A1 | 5/2005 |
| WO | WO2005/106005 A1 | 10/2005 |
| WO | WO2005106005 A1 * | 11/2005 |

OTHER PUBLICATIONS

Ornston et al., 1969, Journal of Bacteriology, 98: 1098-1108.*
Chang et al., 1993, The Journal of Biological Chemistry, 268: 3911-3919.*
Pellicer et al., 1999, The Journal of Biological Chemistry, 274: 1745-1752.*
Jasin et al., 1984, Journal of Bacteriology, 159: 783-786.*
Tani et al., 1987, Agric. Biol. Chem., 42: 63-68.*
Peekhaus et al., 1998, Journal of Bacteriology, 180: 3495-3502.*
Kornberg et al., 1973, Biochem. J. 134: 489-498.*
Cornah et al., 2004, The Journal of Biological Chemistry, vol. 279, No. 41, pp. 42916-42923.*
Oesper et al., 1949, Analytical Chemistry, vol. 21, No. 12, p. 1509-1511.*
Nunez, et al., Biochemical characterization of the 2-ketoacid reductases encoded by ycdW and yiaE genes in *Escherichia coli*, Biochem. J. (2001) 354, pp. 707-715.
Yun, et al., Stereospecific synthesis of (R)-2-hydroxy carboxylic acids using recombinant *E. coli* BL21 overexpressing YiaE from *Escherichia coli* K12 and glucose dehydrogenase from *Bacillus subtilis*. Biotechnol Prog. Mar.-Apr. 2005;21 (2):366-71.
Krampitz and Yarris. Glycolate Formation and Excretion by *Chlorella pyrenoidosa* and Netrium digitus. Plant Physiol. Aug. 1983;72(4):1084-7.
Pellicer, et al. glc locus of *Escherichia coli*: characterization of genes encoding the subunits of glycolate oxidase and the glc regulator protein. J Bacteriol. Apr. 1996;178(7):2051-9.

* cited by examiner

*Primary Examiner* — Shin Lin Chen
(74) *Attorney, Agent, or Firm* — Shweta Chandra; Bozicevic, Field & Francis, LLP

(57) ABSTRACT

The present invention provides a method for the biological production of glycolic acid from a fermentable carbon source in a microorganism. In one aspect of the present invention, a process for the conversion of glucose to glycolic acid is achieved by the use of a recombinant organism comprising a host *E. coli* transformed i) to attenuate the glyoxylate consuming pathways to other compounds than glycolate ii) to use an NADPH glyoxylate reductase to convert glyoxylate to glycolate iii) to attenuate the level of all the glycolate metabolizing enzymes and iv) increase the flux in the glyoxylate pathway. In another aspect of the present invention, the process for the production of glycolic acid from a fermentable carbon source, using a recombinant *E. coli*, is improved by increasing the NADPH availability in the cells. Optionally the glycolic acid produced can be purified through a step of polymerization to at least glycolic acid dimers and recovered by depolymerization from glycolic acid dimers, oligomers and/or polymers.

33 Claims, 2 Drawing Sheets

SEQUENCE LISTING

<160> NUMBER OF SEQ ID NOS: 40

<210> SEQ ID NO 1
<211> LENGTH: 100
<212> TYPE: DNA
<213> ORGANISM: Artificial
<220> FEATURE:
<223> OTHER INFORMATION: PCR primer

<400> SEQUENCE: 1
ggcaacaaca accgatgaac tggctttcac aaggccgtat ggcgagcagg agaagcaaat        60
tcttactgcc gaagcggtag catatgaata tcctccttag                              100

<210> SEQ ID NO 2
<211> LENGTH: 99
<212> TYPE: DNA
<213> ORGANISM: Artificial
<220> FEATURE:
<223> OTHER INFORMATION: PCR primer

<400> SEQUENCE: 2
ggcggtagcc tggcagggtc aggaaatcaa ttaactcatc ggaagtggtg atctgttcca        60
tcaagcgtgc ggcatcgtct gtaggctgga gctgcttcg                               99

<210> SEQ ID NO 3
<211> LENGTH: 24
<212> TYPE: DNA
<213> ORGANISM: Artificial
<220> FEATURE:
<223> OTHER INFORMATION: PCR primer

<400> SEQUENCE: 3
cgttaagcga ttcagcacct tacc                                               24

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4

```
ccagtttctg aatagcttcc                                              20

<210> SEQ ID NO 5
<211> LENGTH: 101
<212> TYPE: DNA
<213> ORGANISM: Artificial
<220> FEATURE:
<223> OTHER INFORMATION: PCR primer

<400> SEQUENCE: 5
ggcaaaaatg agagccgttg acgcggcaat gtatgtgctg gagaaagaag gtatcactac    60
cgccttcggt gttccgggag ctgtaggctg gagctgcttc g                       101

<210> SEQ ID NO 6
<211> LENGTH: 101
<212> TYPE: DNA
<213> ORGANISM: Artificial
<220> FEATURE:
<223> OTHER INFORMATION: PCR primer

<400> SEQUENCE: 6
gcgttacgtt ttaacggtac ggatccatcc agcgtaaacc ggcttccgtg gtggtttggg    60
gtttatattc acacccaacc ccatatgaat atcctcctta g                       101

<210> SEQ ID NO 7
<211> LENGTH: 23
<212> TYPE: DNA
<213> ORGANISM: Artificial
<220> FEATURE:
<223> OTHER INFORMATION: PCR primer

<400> SEQUENCE: 7
ggatatgccc accttgctga agg                                           23

<210> SEQ ID NO 8
<211> LENGTH: 25
<212> TYPE: DNA
<213> ORGANISM: Artificial
<220> FEATURE:
<223> OTHER INFORMATION: PCR primer

<400> SEQUENCE: 8
cgcttagttt caatcgggga aatgg                                         25

<210> SEQ ID NO 9
<211> LENGTH: 99
<212> TYPE: DNA
<213> ORGANISM: Artificial
<220> FEATURE:
<223> OTHER INFORMATION: PCR primer

<400> SEQUENCE: 9
cccagagccg tttacgcatt gacgccaatt ttaaacgttt tgtggatgaa gaagttttac    60
cgggaacagg gctggacgcc atatgaatat cctccttag                          99

<210> SEQ ID NO 10
<211> LENGTH: 99
<212> TYPE: DNA
<213> ORGANISM: Artificial
<220> FEATURE:
<223> OTHER INFORMATION: PCR primer

<400> SEQUENCE: 10
cgcgtaaacg ccaggcgtgt aataacggtt cggtatagcc gtttggctgt ttcacgccga    60
```
ggaagattaa atcgctggct gtaggctgga gctgcttcg                                99

<210> SEQ ID NO 11
<211> LENGTH: 19
<212> TYPE: DNA
<213> ORGANISM: Artificial
<220> FEATURE:
<223> OTHER INFORMATION: PCR primer

<400> SEQUENCE: 11
gccagcaaat ggcgagtgc                                                      19

<210> SEQ ID NO 12
<211> LENGTH: 23
<212> TYPE: DNA
<213> ORGANISM: Artificial
<220> FEATURE:
<223> OTHER INFORMATION: PCR primer

<400> SEQUENCE: 12
cgcagagtat cgttaagatg tcc                                                 23

<210> SEQ ID NO 13
<211> LENGTH: 24
<212> TYPE: DNA
<213> ORGANISM: Artificial
<220> FEATURE:
<223> OTHER INFORMATION: PCR primer

<400> SEQUENCE: 13
ccgacagtaa gacgggtaag cctg                                                24

<210> SEQ ID NO 14
<211> LENGTH: 22
<212> TYPE: DNA
<213> ORGANISM: Artificial
<220> FEATURE:
<223> OTHER INFORMATION: PCR primer

<400> SEQUENCE: 14
agcttagtaa agccctcgct ag                                                  22

<210> SEQ ID NO 15
<211> LENGTH: 43
<212> TYPE: DNA
<213> ORGANISM: Artificial
<220> FEATURE:
<223> OTHER INFORMATION: PCR primer

<400> SEQUENCE: 15
agctagctct catgagaata aatttcgcac aacgcttttc ggg                           43

<210> SEQ ID NO 16
<211> LENGTH: 38
<212> TYPE: DNA
<213> ORGANISM: Artificial
<220> FEATURE:
<223> OTHER INFORMATION: PCR primer

<400> SEQUENCE: 16
gcatgcatcc cgggtctctc ctgtattcaa ttcccgcc                                 38

<210> SEQ ID NO 17
<211> LENGTH: 103
<212> TYPE: DNA

```
<213> ORGANISM: Artificial
<220> FEATURE:
<223> OTHER INFORMATION: PCR primer

<400> SEQUENCE: 17
gcgtcttgat ggcgctttac ccgatgtcga ccgcacatcg gtactgatgg cactgcgtga      60
gcatgtccct ggacttgaga tcccatatga atatcctcct tag                      103

<210> SEQ ID NO 18
<211> LENGTH: 99
<212> TYPE: DNA
<213> ORGANISM: Artificial
<220> FEATURE:
<223> OTHER INFORMATION: PCR primer

<400> SEQUENCE: 18
cgcgtaaacg ccaggcgtgt aataacggtt cggtatagcc gtttggctgt ttcacgccga      60
ggaagattaa atcgctggct gtaggctgga gctgcttcg                            99

<210> SEQ ID NO 19
<211> LENGTH: 20
<212> TYPE: DNA
<213> ORGANISM: Artificial
<220> FEATURE:
<223> OTHER INFORMATION: PCR primer

<400> SEQUENCE: 19
ccaagacaag gtcacagagc                                                  20

<210> SEQ ID NO 20
<211> LENGTH: 23
<212> TYPE: DNA
<213> ORGANISM: Artificial
<220> FEATURE:
<223> OTHER INFORMATION: PCR primer

<400> SEQUENCE: 20
cgcagagtat cgttaagatg tcc                                              23

<210> SEQ ID NO 21
<211> LENGTH: 101
<212> TYPE: DNA
<213> ORGANISM: Artificial
<220> FEATURE:
<223> OTHER INFORMATION: PCR primer

<400> SEQUENCE: 21
ttaagactgt aaataaacca cctgggtctg cagatattca tgcaagccat gtttaccatc      60
tgcgccgcca ataccggatt tcatatgaat atcctcctta g                        101

<210> SEQ ID NO 22
<211> LENGTH: 102
<212> TYPE: DNA
<213> ORGANISM: Artificial
<220> FEATURE:
<223> OTHER INFORMATION: PCR primer

<400> SEQUENCE: 22
atgtcagtac ccgttcaaca tcctatgtat atcgatggac agtttgttac ctggcgtgga      60
gacgcatgga ttgatgtggt agtgtaggct ggagctgctt cg                       102

<210> SEQ ID NO 23
<211> LENGTH: 31
```

<212> TYPE: DNA
<213> ORGANISM: Artificial
<220> FEATURE:
<223> OTHER INFORMATION: PCR primer

<400> SEQUENCE: 23
tgcagcggcg cacgatggcg acgttccgcc g           31

<210> SEQ ID NO 24
<211> LENGTH: 31
<212> TYPE: DNA
<213> ORGANISM: Artificial
<220> FEATURE:
<223> OTHER INFORMATION: PCR primer

<400> SEQUENCE: 24
cacgatgacg accattcatg cctatactgg c           31

<210> SEQ ID NO 25
<211> LENGTH: 101
<212> TYPE: DNA
<213> ORGANISM: Artificial
<220> FEATURE:
<223> OTHER INFORMATION: PCR primer

<400> SEQUENCE: 25
cgcacccatt cccgcgaaac gcggcagaaa acccgccgtt gccaccgcac cagcgactgg     60
acaggttcag tctttaacgc gtgtaggctg gagctgcttc g                        101

<210> SEQ ID NO 26
<211> LENGTH: 100
<212> TYPE: DNA
<213> ORGANISM: Artificial
<220> FEATURE:
<223> OTHER INFORMATION: PCR primer

<400> SEQUENCE: 26
gcgcattcca ccgtacgcca gcgtcacttc cttcgccgct ttaatcacca tcgcgccaaa    60
ctcggtcacg cggtcatcgg catatgaata tcctccttag                          100

<210> SEQ ID NO 27
<211> LENGTH: 26
<212> TYPE: DNA
<213> ORGANISM: Artificial
<220> FEATURE:
<223> OTHER INFORMATION: PCR primer

<400> SEQUENCE: 27
cctttgaggt cgcatggcca gtcggc                 26

<210> SEQ ID NO 28
<211> LENGTH: 33
<212> TYPE: DNA
<213> ORGANISM: Artificial
<220> FEATURE:
<223> OTHER INFORMATION: PCR primer

<400> SEQUENCE: 28 gcttttaat agaggcgtcg ccagctcctt gcc          33

<210> SEQ ID NO 29
<211> LENGTH: 102
<212> TYPE: DNA
<213> ORGANISM: Artificial
<220> FEATURE:

<223> OTHER INFORMATION: PCR primer

<400> SEQUENCE: 29
cgcgcgagac tcgctctgct tatctcgccc ggatagaaca agcgaaaact tcgaccgttc    60
atcgttcgca gttggcatgc ggtgtaggct ggagctgctt cg    102

<210> SEQ ID NO 30
<211> LENGTH: 100
<212> TYPE: DNA
<213> ORGANISM: Artificial
<220> FEATURE:
<223> OTHER INFORMATION: PCR primer

<400> SEQUENCE: 30
gcttagcgcc ttctacagct tcacgcgcca gcttagtaat gcggtcgtaa tcgcccgctt    60
ccagcgcatc tgccggaacc catatgaata tcctccttag    100

<210> SEQ ID NO 31
<211> LENGTH: 29
<212> TYPE: DNA
<213> ORGANISM: Artificial
<220> FEATURE:
<223> OTHER INFORMATION: PCR primer

<400> SEQUENCE: 31
gggtagactc cattactgag gcgtgggcg    29

<210> SEQ ID NO 32
<211> LENGTH: 24
<212> TYPE: DNA
<213> ORGANISM: Artificial
<220> FEATURE:
<223> OTHER INFORMATION: PCR primer

<400> SEQUENCE: 32
ccacatgata ccgggatggt gacg    24

<210> SEQ ID NO 33
<211> LENGTH: 100
<212> TYPE: DNA
<213> ORGANISM: Artificial
<220> FEATURE:
<223> OTHER INFORMATION: PCR primer

<400> SEQUENCE: 33
ccaacgcaga ccgctgcctg gcaggcacta cagaaacact tcgatgaaat gaaagacgtt    60
acgatcgccg atcttttgc tgtaggctgg agctgcttcg    100

<210> SEQ ID NO 34
<211> LENGTH: 100
<212> TYPE: DNA
<213> ORGANISM: Artificial
<220> FEATURE:
<223> OTHER INFORMATION: PCR primer

<400> SEQUENCE: 34
gcgccacgct ttatagcggt taatcagacc attggtcgag ctatcgtggc tgctgatttc    60
tttatcatct ttcagctctg catatgaata tcctccttag    100

<210> SEQ ID NO 35
<211> LENGTH: 30
<212> TYPE: DNA
<213> ORGANISM: Artificial

```
<220> FEATURE:
<223> OTHER INFORMATION: PCR primer

<400> SEQUENCE: 35
gcggggcggt tgtcaacgat ggggtcatgc                                    30

<210> SEQ ID NO 36
<211> LENGTH: 30
<212> TYPE: DNA
<213> ORGANISM: Artificial
<220> FEATURE:
<223> OTHER INFORMATION: PCR primer

<400> SEQUENCE: 36
cggtatgatt tccgttaaat tacagacaag                                    30

<210> SEQ ID NO 37
<211> LENGTH: 100
<212> TYPE: DNA
<213> ORGANISM: Artificial
<220> FEATURE:
<223> OTHER INFORMATION: PCR primer

<400> SEQUENCE: 37
cccagaatct cttttgtttc ccgatggaac aaaattttca gcgtgcccac gttcatgccg   60
acgatttgtg cgcgtgccag tgtaggctgg agctgcttcg                         100

<210> SEQ ID NO 38
<211> LENGTH: 100
<212> TYPE: DNA
<213> ORGANISM: Artificial
<220> FEATURE:
<223> OTHER INFORMATION: PCR primer

<400> SEQUENCE: 38
ggtgcgcgcg tcgcagttat cgagcgttat caaaatgttg gcggcggttg cacccactgg   60
ggcaccatcc cgtcgaaagc catatgaata tcctccttag                         100

<210> SEQ ID NO 39
<211> LENGTH: 20
<212> TYPE: DNA
<213> ORGANISM: Artificial
<220> FEATURE:
<223> OTHER INFORMATION: PCR primer

<400> SEQUENCE: 39
gatgctggaa gatggtcact                                               20

<210> SEQ ID NO 40
<211> LENGTH: 18
<212> TYPE: DNA
<213> ORGANISM: Artificial
<220> FEATURE:
<223> OTHER INFORMATION: PCR primer

<400> SEQUENCE: 40
gtgaatgaac ggtaacgc                                                 18
```

GLYCOLIC ACID PRODUCTION BY FERMENTATION FROM RENEWABLE RESOURCES

FIELD OF INVENTION

The invention comprises a process for the bioconversion of a fermentable carbon source to glycolic acid by an aerobically-grown microorganism.

BACKGROUND OF THE INVENTION

Glycolic acid ($HOCH_2COOH$) is the first member of the alpha-hydroxy acid family of carboxylic acids. Glycolic acid has dual functionality with both alcohol and moderately strong acid functional groups on a very small molecule. This results in unique chemical attributes as well as typical acid and alcohol chemistry.

Glycolic acid uses both the hydroxyl and carboxylic acid groups to form five-member ring complexes (chelates) with polyvalent metals. This metal ion complexing ability is useful in dissolution of hard water scale and prevention of deposition, especially in acid cleaning applications where good rinsibility is a key factor. Glycolic acid undergoes reactions with organic alcohols and acids to form esters. Low molecular weight alkyl glycolic esters have unusual solvency properties and may be used as a substitute for n- and iso-propanol, ethylenediamine, phenol, m-cresol, 2-ethoxyethyl acetate, and ethyl and methyl lactate. Higher molecular weight alkyl esters can be used in personal care product formulations. Glycolic acid can react with itself to form dimeric glycolide, head-to-tail polyester oligomers, and long-chain polymers. Copolymers can be made with other alpha hydroxy acids like lactic acid. The polyester polymers gradually hydrolyze in aqueous environments at controllable rates. This property makes them useful in biomedical applications such as dissolvable sutures and in applications where a controlled release of acid is needed to reduce pH. Currently more than 15,000 tons of glycolic acid are consumed annually in the United states.

The biological production of glycolic acid, presented in FIG. 1, requires the formation of glyoxylate as an intermediate which is reduced to glycolate by a NADPH dependent oxidoreductase encoded by the gene ycdW (Nunez et al, (2001) Biochemistry, 354, 707-715). Glyoxylate is an intermediate of the glyoxylate cycle (Tricarboxylic acid cycle and glyoxylate bypass, reviewed in Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli* and *Salmonella*: Cellular and Molecular Biology. American Society for Microbiology). In this cycle isocitrate is cleaved into succinate and glyoxylate, a reaction that is catalyzed by isocitrate lyase, encoded by the aceA gene. Succinate directly enters the citric acid cycle and is converted into oxaloacetate. Glyoxylate is converted into malate by incorporating a molecule of acetyl-CoA derived from acetate a reaction catalyzed by the two malate synthase isoenzymes encoded by aceB and gclB. The entry of carbon into the glyoxylate shunt is regulated on the transcriptional and posttranscriptional level. Transcriptional regulation is exerted on the aceBAK operon by the IclR repressor. AceBAK encode malate synthase, isocitrate lyase and isocitrate kinase/phosphatase, respectively. The iclR gene is negatively autoregulated and activated by the FadR protein. The activity of isocitrate dehydrogenase, encoded by the icd gene, is regulated posttranscriptionally. Isocitrate dehydrogenase and isocitrate lyase compete for the common substrate isocitrate. Since the $K_m$ value for isocitrate is significantly higher for the isocitrate lyase reaction, the entry into the glyoxylate pathway depends in part on the regulation of the isocitrate dehydrogenase enzyme. Isocitrate dehydrogenase activity is modulated by its phosphorylation or dephosphorylation catalyzed by AceK. Phosphorylation reduces the activity of Icd and dephosphorylation reactivates the Icd enzyme. If AceK acts as kinase or phosphatase depends on the presence of several metabolites. Depletion of isocitrate and 3-phosphoglycerate stimulates kinase activity; the presence of pyruvate and AMP inhibits the kinase function thus favoring the phosphatase activity (see also Neidhard). Glyoxylate can be converted to tartronate semialdehyde by a glyoxylate carboligase encoded by gcl and to 2-keto-4-hydroxy glutarate by a 2-keto-3-deoxygluconate 6-phosphate aldolase encoded by eda while glycolate can be reduced to glycoaldehyde by a $NAD^+$ dependent glycoaldehyde dehydrogenase encoded by aldA or oxidized to glyoxylate by a $NAD^+$ dependent glycolate oxidase encoded by glcDEF.

The problem to be solved by the present invention is the biological production of glycolic acid from an inexpensive carbon substrate such as glucose or other sugars. The number of biochemical steps and the complexity of the metabolic pathways necessitate, for an industrial feasible process of glycolic acid production, the use of a metabolically engineered whole cell catalyst.

SUMMARY OF THE INVENTION

Applicants have solved the stated problem and the present invention provides a method for bioconverting a fermentable carbon source directly to glycolic acid. Glucose is used as a model substrate and recombinant *E. coli* is used as the model host. In one aspect of this invention, recombinant *E. coli* unable to metabolize glyoxylate to other compounds than glycolate are constructed by inactivating the genes coding for the malate synthases (aceB and glcB), the glyoxylate carboligase (gcl) and the 2-keto-3-deoxygluconate 6-phosphate aldolase (eda). In another aspect of this invention, an NADPH dependant glyoxylate reductase activity is used to reduce the toxic glyoxylate into glycolate by using endogenous encoding genes like ycdW or yiaE. In a further aspect of this invention the gene encoding the glycolate metabolizing enzymes, glycolate oxidase (glcDEF) and glycoaldehyde dehydrogenase (aldA) are deleted. Furthermore, the flux in the glyoxylate pathway is increased by i) increasing the level of aceA by inactivating the iciR gene or directly increasing the expression of aceA, ii) decreasing the expression level or inactivating the gene encoding the isocitrate dehydrogenase (icd) and iii) inactivating the genes encoding the pyruvate oxidase (poxB) and the acetate pathway (ack, pta). In a final aspect of this invention, a better yield of glycolate production is obtained by increasing NADPH availability by inactivating the genes encoding the glucose-6-phosphate isomerase (pgi), the 6-phosphogluconate dehydratase (edd) and the soluble transhydrogenase (udhA). The present invention may be generally applied to include any carbon substrate that is readily converted to acetyl-coA.

Accordingly it is an object of the present invention to provide a recombinant organism, useful for the production of glycolic acid comprising: (a) at least inactivation of all the malate synthases, glyoxylate carboligases and 2-keto-3-deoxygluconate 6-phosphate aldolase encoding genes; (b) at least one gene encoding a polypeptide having NADPH dependent glyoxylate reductase activity and (c) at least inactivation of the genes encoding $NAD^+$ dependant glycolate oxidation to glyoxylate. Optionally the recombinant organism may comprise i) inactivating mutations in endogenous genes selected from the group consisting of: (a) a gene encoding a repressor of the glyoxylate pathway (b) a gene encoding a polypeptide having glucose-6-phosphate isomerase activity. (c) a gene encoding a polypeptide having soluble transhydrogenase activity. (d) a gene encoding a polypeptide having 6-phosphogluconate dehydratase activity (e) genes encoding polypeptides having phospho-transacetylase and acetate kinase activities. (f) a gene encoding pyruvate oxidase activity (g) a gene encoding glycoaldehyde dehydrogenase activity ii) increase level of a gene encoding isocitrate lyase and iii) decrease level or inactivation of a gene encoding polypeptide having isocitrate dehydrogenase activity.

In another embodiment the invention provides a process for the production of glycolic acid from a recombinant organism comprising: (a) contacting the recombinant organism of the present invention with at least one carbon source selected from the group consisting of monosaccharides, oligosaccharides, polysaccharides, and single-carbon substrates whereby glycolate is produced; optionally (b) recovering the glycolic acid produced in (a) through a step of polymerization to at least glycolic acid dimers and (c) recovery of glycolic acid by depolymerisation from glycolic acid dimmers, oligomers and/or polymers.

BRIEF DESCRIPTION OF THE DRAWINGS

The accompanying drawings which are incorporated in and constitute a part of this specification exemplify the invention and together with the description, serve to explain the principles of this invention.

DETAILED DESCRIPTION OF THE INVENTION

Figure 1:
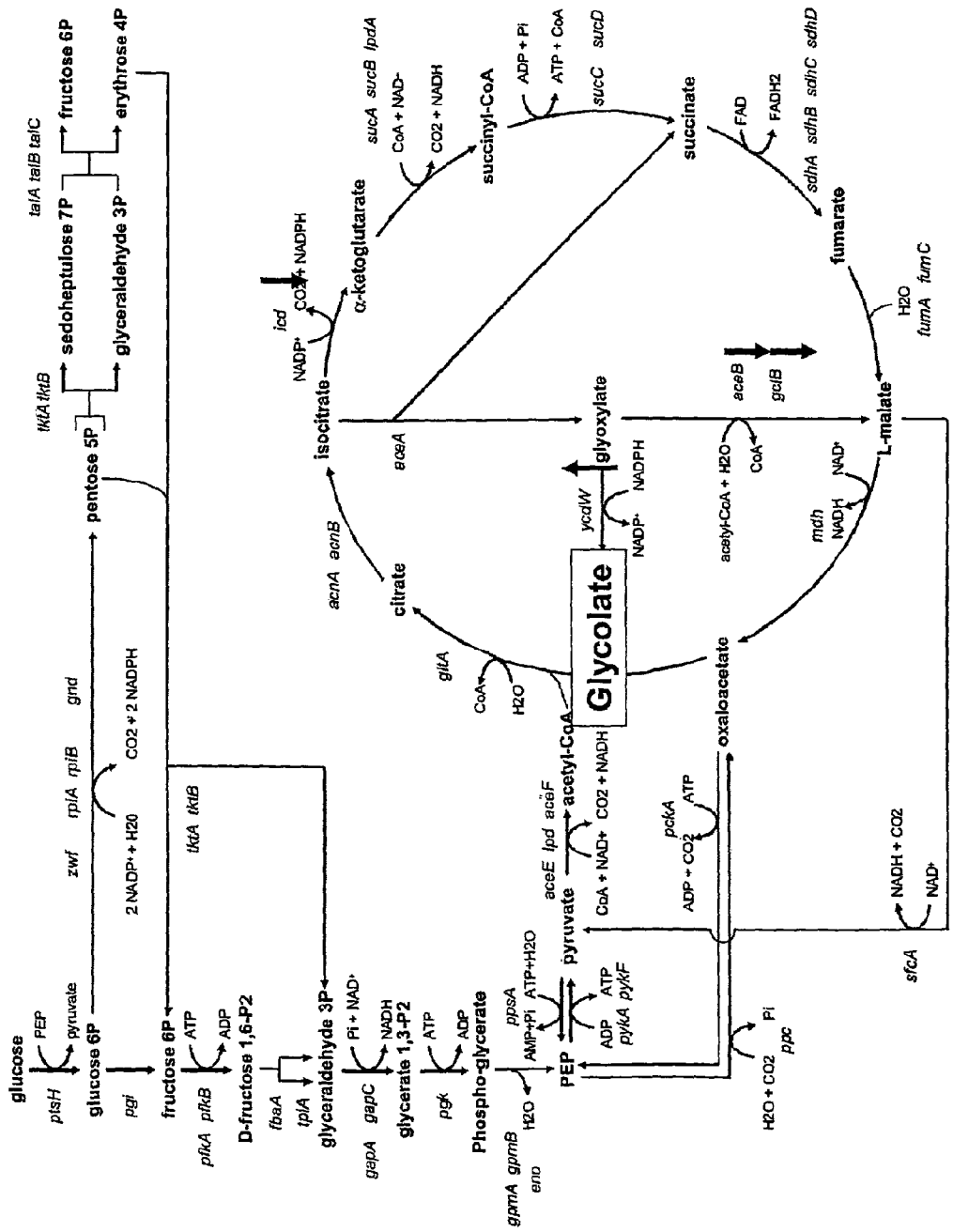
FIG. 1 depicts the genetic engineering of glycolysis, TCA cycle and glyoxylate pathway in the development of glycolic acid production system from carbohydrates.
Figure 2:
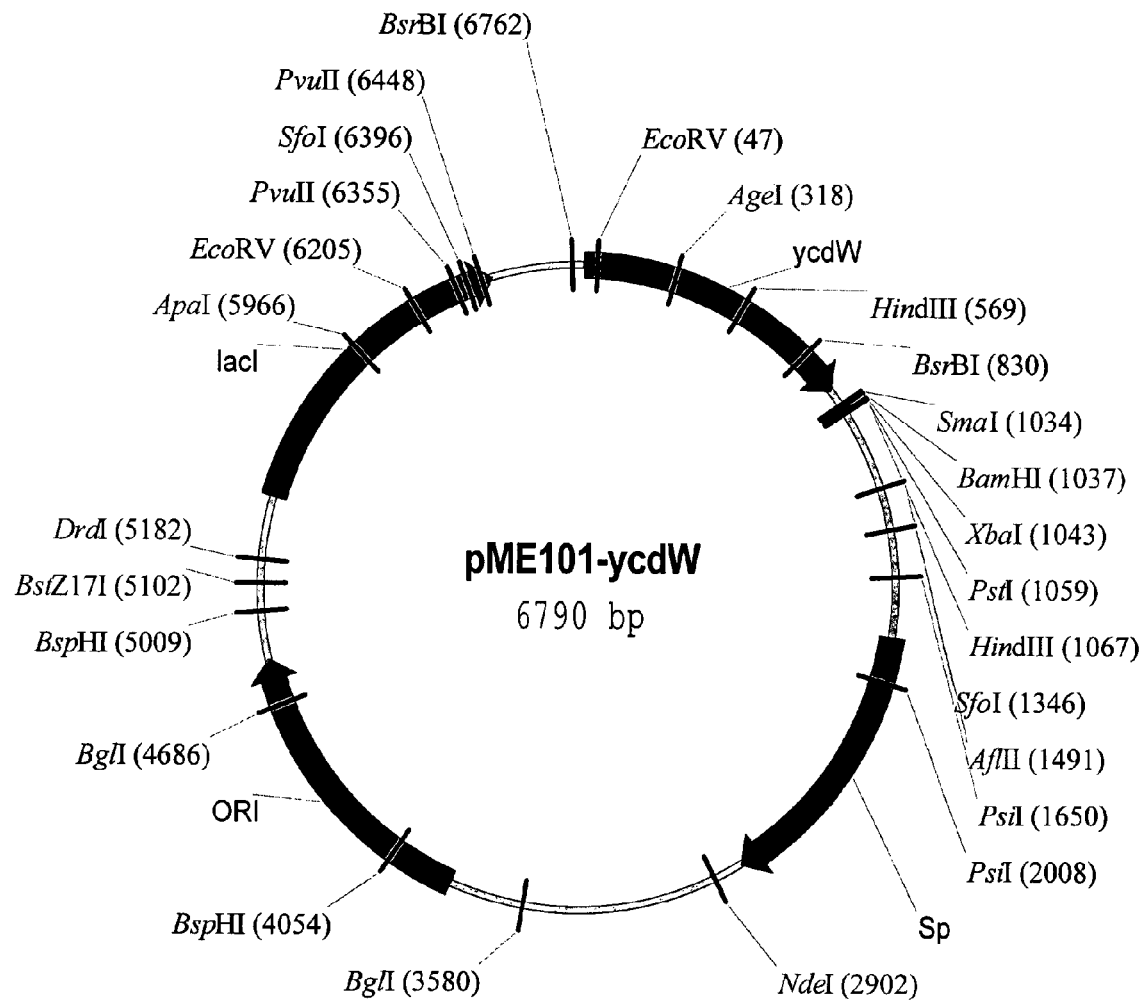
FIG. 2 is a diagram showing the construction of the vector pME101-ycdW.

As used herein the following terms may be used for interpretation of the claims and specification.

The term "mutant strain" refers to a non-wild type strain.

The term "microorganism" refers to all kind of unicellular organisms, including procaryotic organisms like bacteria, and eucaryotic organisms like yeasts. Bacteria include in particular: Enterobacteriaceae, Bacillaceae, Streptomycetaceae and Corynebacteriaceae. Enterobacteriaceae comprise in particular but not exclusively the genera *Escherichia, Klebsiella, Salmonella* and *Pantoea*.

The term "transformation" or "transfection" refers to the acquisition of new genes in a cell after the incorporation of exogenous nucleic acid. The term "transformant" refers to the product of a transformation. The term "genetically altered" refers to the process of changing hereditary material by transformation or mutation.

The term "attenuation" refers to a decreased expression of a gene or a decreased activity of the protein, product of the gene. The man skilled in the art knows numerous means to obtain this result, and for example:

Introduction of a mutation into the gene, decreasing the expression level of this gene, or the level of activity of the encoded protein.

Replacement of the natural promoter of the gene by a low strength promoter, resulting in a lower expression.

Use of elements destabilizing the corresponding messenger RNA or the protein

Deletion of the gene if no expression is needed.

The term "expression" refers to the transcription and translation from a gene to the protein, product of the gene.

The term "plasmid" or "vector" as used herein refers to an extra chromosomal element often carrying genes which are not part of the central metabolism of the cell, and usually in the form of circular double-stranded DNA molecules.

The term "carbon substrate" or "carbon source" means any carbon source capable of being metabolized by a microorganism wherein the substrate contains at least one carbon atom. Authors refer particularly to renewable, inexpensive and fermentable carbon sources such as monosaccharides, oligosaccharides, polysaccharides, single-carbon substrates, and polyols such as glycerol. Single carbon substrate are defined as carbon molecules that contain only one carbon atom such as methanol. Monosaccharides of the formula $(CH_2O)_n$ are also called oses or "simple sugars"; monosaccharides include saccharose, fructose, glucose, galactose and mannose. Other carbon sources comprising more than one monosaccharide are called disaccharides, trisaccharides, oligosaccharides and polysaccharides. Disaccharides include saccharose (sucrose), lactose and maltose. Starch and hemicellulose are polysaccharides, also known as "complex sugars". Therefore the term "carbon source" means any product as cited above, and mixtures thereof.

The term "ATCC" will stand for the American Type Culture Collection, 12301 Parklawn Drive, Rockville, Md. 20852, U.S.A.

The terms "glyoxylate" and "glyoxylic acid" are used interchangeably.

The terms "glycolate" and "glycolic acid" are used interchangeably.

In the description of the present invention, enzymes are identified by their specific activities. This definition thus includes all polypeptides that have the defined specific activity also present in other organisms, more particularly in other microorganisms. Often enzymes with similar activities can be identified by their grouping to certain families defined as PFAM or COG.

PFAM (protein families database of alignments and hidden Markov models; http://www.sanger.ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; http://www.ncbi.nlm.nih.gov/COG/) are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website http://www.ncbi.nlm.nih.gov/BLAST/ with the default parameters indicated on that website. The sequences obtained can then be exploited (e.g., aligned) using, for example, the programs CLUSTALW (http://www.ebi.ac.uk/clustalw/) or MULTALIN (http://prodes.toulouse.inra.fr/multalin/cgi-bin/multalin.pl), with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, N.Y.).

The present invention provides a method for the fermentative production of glycolic acid, its derivatives or precursors, by culturing a microorganism in an appropriate culture medium comprising a carbon source and the recovery of glycolic acid from the culture medium.

A further embodiment of the invention provides a method wherein the microorganism is modified to have a low capacity of glyoxylate conversion, except to produce glycolate, due to the attenuation of genes encoding for enzymes consuming glyoxylate, a key precursor of glycolate: aceB and gclB genes encoding malate synthases, gcl encoding glyoxylate carboligase and eda encoding 2-keto-3-deoxygluconate 6-phosphate aldolase.

In another embodiment of the invention, the microorganism contains at least one gene encoding a polypeptide catalyzing the conversion of glyoxylate to glycolate.

In particular, a gene encoding a NADPH dependent glyoxylate reductase enzyme is present to convert, under aerobic conditions, the toxic glyoxylate intermediate to the low toxicity final product glycolate. The gene can be exogenous or endogenous and can be expressed chromosomally or extrachromosomally. An NADPH-dependant glyoxylate reductase encoding gene can be taken among the ycdW or yiaE genes from the genome of *E. coli* MG1655. In a preferred embodiment, the expression of at least one of said genes is increased. If needed a high level of NADPH-dependant glyoxylate reductase activity can be obtained from chromosomally located genes by using one or several copies on the genome that can be introduced by methods of recombination known to the expert in the field. For extrachromosomal genes, different types of plasmids that differ with respect to their origin of replication and thus their copy number in the cell can be used. They may be present as 1-5 copies, ca 20 or up to 500 copies corresponding to low copy number plasmids with tight replication (pSC101, RK2), low copy number plasmids (pACYC, pRSF1010) or high copy number plasmids (pSK bluescript II). The ycdW or yiaE genes may be expressed using promoters with different strength that need or need not to be induced by inducer molecules. Examples are the promoters Ptrc, Ptac, Plac, the lambda promoter cI or other promoters known to the expert in the field. Expression of the genes may also be boosted by elements stabilizing the corresponding messenger RNA (Carrier and Keasling (1998) Biotechnol. Prog. 15, 58-64) or the protein (e.g. GST tags, Amersham Biosciences).

In a further embodiment of the invention, the microorganism is modified in such a way that it is unable to substantially metabolize glycolate. This result can be achieved by the attenuation of at least one of the genes encoding for enzymes consuming glycolate (glcDEF encoding glycolate oxidase and aldA encoding glycoaldehyde dehydrogenase). Attenuation of genes can be done by replacing the natural promoter by a low strength promoter or by element destabilizing the corresponding messenger RNA or the protein. If needed, complete attenuation of the gene can also be achieved by a deletion of the corresponding DNA sequence.

In another embodiment, the microorganism used in the method of the invention is transformed to increase the glyoxylate pathway flux.

The flux in the glyoxylate pathway may be increased by different means, and in particular:
  i) decreasing the activity of the enzyme isocitrate dehydrogenase (Icd),
  ii) decreasing the activity of at least one of the following enzymes:
    phospho-transacetylase, encoded by the pta gene
    acetate kinase, encoded by the ack gene
    pyruvate oxidase, encoded by the poxB gene by attenuation of the genes,
  iii) increasing the activity of the enzyme isocitrate lyase, encoded by the aceA gene.

Decreasing the level of isocitrate dehydrogenase can be accomplished by introducing artificial promoters that drive the expression of the icd gene, coding for the isocitrate dehydrogenase, or by introducing mutations into the icd gene that reduce the enzymatic activity of the protein.

Since the activity of the protein Icd is reduced by phosphorylation, it may also be controlled by introducing mutant aceK genes that have increased kinase activity or reduced phosphatase activity compared to the wild type AceK enzyme.

Increasing the activity of the isocitrate lyase can be accomplished either by attenuating the level of iclR or fadR genes, coding for glyoxylate pathway repressors, either by stimulating the expression of the aceA gene, for example by introducing artificial promoters that drive the expression of the gene, or by introducing mutations into the aceA gene that increase the activity the encoded protein.

An embodiment of the invention provides a better yield of glycolate production by increasing NADPH availability to the NADPH-dependant glyoxylate reductase. This modification of the microorganism characteristics can be obtained through the attenuation of at least one of the genes selected among the following: pgi encoding the glucose-6-phosphate isomerase, udhA encoding the soluble transhydrogenase and edd encoding the 6-phosphogluconate dehydratase activity. With such genetic modifications, all the glucose-6-phosphate will have to enter glycolysis through the pentose phosphate pathway and 2 NADPH will be produced per glucose-6-phosphate metabolized.

In another embodiment the invention provides a process for the fermentative production of glycolic acid from a recombinant organism comprising: (a) contacting the recombinant organism of the present invention with at least one carbon source selected from the group consisting of glucose, sucrose, monosaccharides, oligosaccharides, polysaccharides, starch or its derivatives, glycerol and single-carbon substrates whereby glyoxylic acid is produced. Optionally the process comprises a step of concentration of glycolate in the bacteria or in the medium and isolation of glycolic acid from the fermentation broth and/or the biomass optionally remaining in portions or in the total amount (0-100%) in the end product. Optionally the process comprises a step of recovery of the glycolic acid produced in step (a) through a step of polymerization to at least glycolic acid dimers and (b) recovery of glycolic acid by depolymerisation from glycolic acid dimers, oligomers and/or polymers.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

The fermentation is generally conducted in fermenters with an inorganic culture medium of known defined composition adapted to the bacteria used, containing at least one simple carbon source, and if necessary a co-substrate necessary for the production of the metabolite.

The invention is also related to the microorganism as described previously. Preferably, this microorganism is selected among the group consisting of *E. coli, C. glutamicum* or *S. cerevisiae*.

Example 1

Construction of Strains Unable to Metabolize Glyoxylate Except to Reduce it to Glycolate: MG1655 ΔaceB Δgcl ΔglcB To delete the aceB gene the homologous recombination strategy described by Datsenko & Wanner (2000) is used. This strategy allows the insertion of a chloramphenicol or a kanamycin resistance cassette, while deleting most of the genes concerned. For this purpose the following oligonucleotides are used:

DaceBF
(SEQ ID NO 1)
ggcaacaacaaccgatgaactggctttcacaaggccgtatggcgagcagg agaagcaaattcttactgccgaagcggtagCATATGAATATCCTCCTTAG with
- a region (lower case) homologous to the sequence (4213068-4213147) of the gene aceB (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645), DaceBR
(SEQ ID NO 2))
ggcggtagcctggcagggtcaggaaatcaattaactcatcggaagtggtg atctgttccatcaagcgtgcggcatcgtcTGTAGGCTGGAGCTGCTTCG with
- a region (lower case) homologous to the sequence (4214647-4214569) of the gene aceB (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645).

The oligonucleotides DaceBF and DaceBR are used to amplify the chloramphenicol resistance cassette from the plasmid pKD3. The PCR product obtained is then introduced by electroporation into the strain MG1655 (pKD46), in which the Red recombinase enzyme expressed permits the homologous recombination. The chloramphenicol resistant transformants are then selected and the insertion of the resistance cassette is verified by a PCR analysis with the oligonucleotides aceBF and aceBR defined below. The strain retained is designated MG1655 ΔaceB::Cm aceBF
(SEQ ID NO 3):
cgttaagcgattcagcaccttacc (homologous to the sequence from 4212807 to 4212830).

aceBR
(SEQ ID NO 4):
ccagtttctgaatagcttcc (homologous to the sequence from 4215327 to 4215308).

Then, the gcl gene is deleted in the MG1655 ΔaceB::Cm strain by transduction. The MG1655 Δgcl::Km strain is first constructed using the same method as previously described with the following oligonucleotides:

DgclF
(SEQ ID NO 5)
ggcaaaaatgagagccgttgacgcggcaatgtatgtgctggagaaagaag gtatcactaccgccttcggtgttccgggagcTGTAGGCTGGAGCTGCTTC

G with
- a region (lower case) homologous to the sequence (533142-533224) of the region of the gene gcl (reference sequence on the website http://genolist.pasteur.fr/Colibri/),
- a region (upper case) for the amplification of the kanamycin resistance cassette (reference sequence in Datsenko, K. A. & Wanner, B. L., 2000, PNAS, 97: 6640-6645), DgipR
(SEQ ID NO 6)
gcgttacgttttaacggtacggatccatccagcgtaaaccggcttccgtg gtggtttgggtttatattcacacccaacccCATATGAATATCCTCCTTA

G with
- a region (lower case) homologous to the sequence (535720-535640) of the region of the gene gcl (reference sequence on the website http://genolist.pasteur.fr/Colibri/),
- a region (upper case) for the amplification of the kanamycin resistance cassette (reference sequence in Datsenko, K. A. & Wanner, B. L., 2000, PNAS, 97: 6640-6645).

The oligonucleotides DgclF and DgipR are used to amplify the kanamycin resistance cassette from the plasmid pKD4. The PCR product obtained is then introduced by electroporation into the strain MG1655 (pKD46). The kanamycin resistant transformants are then selected and the insertion of the resistance cassette is verified by a PCR analysis with the oligonucleotides gclF and gipR defined below. The strain retained is designated MG1655 Δgcl::Km.

gclF
(SEQ ID NO 7):
ggatatgcccaccttgctgaagg (homologous to the sequence from 532795 to 532817).

gipR
(SEQ ID NO 8):
cgcttagtttcaatcggggaaatgg (homologous to the sequence from 536114 to 536090).

To transfer the deletion Δgcl::Km, the method of phage P1 transduction is used. The protocol followed is implemented in 2 steps with the preparation of the phage lysate of the strain MG1655 Δgcl::Km and then transduction into strain MG1655 ΔaceB::Cm. The construction of the strain is described above.

Preparation of phage lysate P1:

Inoculation with 100 µl of an overnight culture of the strain MG1655 Δgcl::Km of 10 ml of LB+Km 50 µg/ml+ glucose 0.2%+CaCl$_2$ 5 mM.

Incubation for 30 min at 37° C. with shaking.

Addition of 100 µl of phage lysate P1 prepared on the strain MG1655 (about 1.10$^9$ phage/ml).

Shaking at 37° C. for 3 hours until all the cells were lysed.

Addition of 200 µl chloroform and vortexing.

Centrifugation for 10 min at 4500 g to eliminate cell debris.

Transfer of supernatant to a sterile tube and addition of 200 µl chloroform.

Storage of lysate at 4° C.

Transduction

Centrifuging for 10 min at 1500 g of 5 ml of an overnight culture of the strain MG1655 ΔaceB::Cm in LB medium.

Suspension of the cell pellet in 2.5 ml of 10 mM MgSO$_4$, 5 mM CaCl$_2$

Control tubes: 100 µl cells
100 µl phages P1 of strain MG1655 Δgcl::Km

Test tube: 100 µl of cells+100 µl of phages P1 of the strain MG1655 Δgcl::Km.

Incubation for 30 min at 30° C. without shaking.

Addition of 100 µl of 1 M sodium citrate in each tube and vortexing.

Addition of 1 ml of LB.

Incubation for 1 hour at 37° C. with shaking.

Spreading on dishes LB+Km 50 µg/ml after centrifuging of tubes for 3 min at 7000 rpm.

Incubation at 37° C. overnight.

Verification of the Strain

The kanamycin resistant transformants are then selected and the deletion of the gene Δgcl::Km is verified by a PCR analysis with the oligonucleotides gclF and gipR previously described. The strain retained is designated MG1655 ΔaceB::Cm Δgcl::Km.

The kanamycin and chloramphenicol resistance cassettes can then be eliminated. The plasmid pCP20 carrying FLP recombinase acting at the FRT sites of the kanamycin and the chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (aceBF/aceBR and gclF/gipR). The strain retained is designated MG1655 ΔaceB Δgcl.

Then, the glcB gene is deleted in the MG1655 ΔaceB Δgcl strain by transduction. The MG1655 ΔglcB::Km is first constructed using the same method as previously described with the following oligonucleotides DglcBR
(SEQ ID NO 9)
cccagagccgtttacgcattgacgccaattttaaacgttttgtggatgaa gaagttttaccgggaacagggctggacgcCATATGAATATCCTCCTTAG with
a region (lower case) homologous to the sequence (3121805-3121727) of the region of the gene glcB (reference sequence on the website http://genolist.pasteur.fr/Colibri/),
a region (upper case) for the amplification of the kanamycin resistance cassette (reference sequence in Datsenko, K. A. & Wanner, B. L., 2000, PNAS, 97: 6640-6645), DglcBF
(SEQ ID NO 10)
cgcgtaaacgccaggcgtgtaataacggttcggtatagccgtttggctgt ttcacgccgaggaagattaaatcgctggcTGTAGGCTGGAGCTGCTTCG with
a region (lower case) homologous to the sequence (3119667-3119745) of the region of the gene glcB (reference sequence on the website http://genolist.pasteur.fr/Colibri/),
a region (upper case) for the amplification of the kanamycin resistance cassette (reference sequence in Datsenko, K. A. & Wanner, B. L., 2000, PNAS, 97: 6640-6645).

The oligonucleotides DglcBF and DglcBR are used to amplify the kanamycin resistance cassette from the plasmid pKD4. The PCR product obtained is then introduced by electroporation into the strain MG1655 (pKD46). The kanamycin resistant transformants are then selected and the insertion of the resistance cassette is verified by a PCR analysis with the oligonucleotides glcBF and glcBR defined below. The strain retained is designated MG1655 ΔglcB::Km.

glcBR
(SEQ ID NO 11):
gccagcaaatggcgagtgc (homologous to the sequence from 3122225 to 3122207).

glcBF
(SEQ ID NO 12):
cgcagagtatcgttaagatgtcc (homologous to the sequence from 3119475 to 3119497).

To transfer the deletion ΔglcB::Km, the method of phage P1 transduction is used. The preparation of the phage lysate of the strain MG1655 ΔglcB::Km is used for the transduction into strain MG1655 ΔaceB Δgcl.

The kanamycin resistant transformants are then selected and the deletion of the gene ΔglcB::Km is verified by a PCR analysis with the previously defined oligonucleotides glcBF and glcBR. The strain retained is designated MG1655 ΔaceB Δgcl ΔglcB::Km.

The kanamycin resistance cassette can then be eliminated. The plasmid pCP20 carrying FLP recombinase acting at the FRT sites of the kanamycin resistance cassette is then introduced into the recombinant sites by electroporation. After a series of cultures at 42° C., the loss of the kanamycin resistance cassette is verified by a PCR analysis with the same oligonucleotides as used previously (glcBF and glcBR). The strain retained is designated MG1655 ΔaceB Δgcl ΔglcB.

Example 2

Construction of Strains with Increased Level of NADPH Dependent Glyoxylate Reductase: MG1655 ΔaceB Δgcl ΔglcB (pME101-ycdW)

To boost the level of NADPH dependant glyoxylate reductase the ycdW gene is expressed from the plasmid pCL1920 (Lerner & Inouye, 1990, NAR 18, 15 p 4631) using the promoter Ptrc. For the expression from a low copy vector the plasmid pME101 is constructed as follows. The plasmid pCL1920 is PCR amplified using the oligonucleotides PME101F and PME101R and the BstZ17I-XmnI fragment from the vector PTRC99A harboring the lacI gene and the P$_{trc}$ promoter is inserted into the amplified vector.

```
PME101F
                                     (SEQ ID NO 13):
Ccgacagtaagacgggtaagcctg PME101R
                                     (SEQ ID NO 14):
Agcttagtaaagccctcgctag
```

The ycdW gene is PCR amplified from genomic DNA using the following oligonucleotides:

```
BspHI ycdW
                                     (SEQ ID NO 15):
agctagctct catgag aataaatttcgcacaacgcttttcggg SmaI ycdW
                                     (SEQ ID NO 16):
gcatgcat cccggg tctctcctgtattcaattcccgcc
```

The PCR fragment is digested with BspHI and SmaI and cloned into the vector pME101 cut by the NcoI and SmaI restriction enzymes resulting in plasmid pME101-ycdW.

The pME101-ycdW plasmid is then introduced in the strain MG1655 ΔaceB Δgcl ΔglcB.

Example 3

Construction of Strains with Decreased Consumption of Glycolate: MG1655 ΔaceB Δgcl ΔglcDEFGB ΔaldA (pME101-ycdW)

The glcDEFGB genes are deleted in the MG1655 ΔaceB Δgcl strain by transduction.
The MG1655 ΔglcDEFGB::Km is first constructed using the same method as previously described with the following oligonucleotides

```
DglcDR
                                     (SEQ ID NO 17)
gcgtcttgatggcgctttacccgatgtcgaccgcacatcggtactgatgg cactgcgtgagcatgtccctggacttgagatccCATATGAATATCCTCCT
TAG
``` with
- a region (lower case) homologous to the sequence (3126016-3125934) of the gene glcD (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645),

```
DglcBF
                                     (SEQ ID NO 18)
cgcgtaaacgccaggcgtgtaataacggttcggtatagccgtttggctgt ttcacgccgaggaagattaaatcgctggcTGTAGGCTGGAGCTGCTTCG
``` with
- a region (lower case) homologous to the sequence (3119667-3119745) of the region of the gene glcB (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645).

The oligonucleotides DglcDR and DglcBF are used to amplify the kanamycin resistance cassette from the plasmid pKD4. The PCR product obtained is then introduced by electroporation into the strain MG1655 (pKD46), in which the Red recombinase enzyme expressed permits the homologous recombination. The chloramphenicol resistant transformants are then selected and the insertion of the resistance cassette is verified by a PCR analysis with the oligonucleotides glcDR and glcBF defined below. The strain retained is designated MG1655 ΔglcDEFGB::Km

```
glcDR
                                     (SEQ ID NO 19):
ccaagacaaggtcacagagc (homologous to the sequence from 3126183 to 3126164).

glcBF
                                     (SEQ ID NO 20):
cgcagagtatcgttaagatgtcc (homologous to the sequence from 3119475 to 3119497).
```

To transfer the deletion ΔglcDEFGB::Km, the method of phage P1 transduction is used. The preparation of the phage lysate of the strain MG1655 ΔglcDEFGB::Km is used for the transduction into strain MG1655 ΔaceB Δgcl.

The kanamycin resistant transformants are then selected and the deletion of the gene ΔglcDEFGB::Km is verified by a PCR analysis with the previously defined oligonucleotides glcBF and glcDR. The strain retained is designated MG1655 ΔaceB Δgcl ΔglcDEFGB::Km.

Then, the aldA gene is deleted in the MG1655 ΔaceB Δgcl ΔglcDEFGB::Km strain by transduction. The MG1655 aldA::Cm is first constructed using the same method as previously described with the following oligonucleotides:

```
AldA D r
                                     (SEQ ID NO 21)
ttaagactgtaaataaaccacctgggtctgcagatattcatgcaagccat gtttaccatctgcgccgccaataccggatttCATATGAATATCCTCCTTA
G
``` with
- a region (lower case) homologous to the sequence (1487615 to 1487695) of the gene aldA (reference sequence on the website http://genolist.pasteur.fr/Colibri/),
- a region (upper case) for the amplification of the kanamycin resistance cassette (reference sequence in Datsenko, K. A. & Wanner, B. L., 2000, PNAS, 97: 6640-6645),

```
AldA D f
                                     (SEQ ID NO 22)
atgtcagtacccgttcaacatcctatgtatatcgatggacagtttgttac ctggcgtggagacgcatggattgatgtggtaGTGTAGGCTGGAGCTGCTT
CG
``` with
- a region (lower case) homologous to the sequence (1486256 to 1486336) of the gene aldA (reference sequence on the website http://genolist.pasteur.fr/Colibri/),
- a region (upper case) for the amplification of the kanamycin resistance cassette (reference sequence in Datsenko, K. A. & Wanner, B. L., 2000, PNAS, 97: 6640-6645).

The oligonucleotides aldAF and aldAR are used to amplify the chloramphenicol resistance cassette from the plasmid pKD3. The PCR product obtained is then introduced by electroporation into the strain MG1655 (pKD46), in which the Red recombinase enzyme expressed permits the homologous recombination. The kanamycin resistant transformants are then selected and the insertion of the resistance cassette is verified by a PCR analysis with the oligonucleotides YdcFCf and gapCCR defined below. The strain retained is designated MG1655 ΔaldA::Cm.

YdcFCf
(SEQ ID NO 23):
tgcagcggcgcacgatggcgacgttccgccg (homologous to the sequence from 1485722 to 1485752).

gapCCR
(SEQ ID NO 24):
cacgatgacgaccattcatgcctatactggc (homologous to the sequence from 1488195 to 1488225).

To transfer the deletion ΔaldA::Cm, the method of phage P1 transduction is used. The preparation of the phage lysate of the strain MG1655 ΔaldA::Cm is used for the transduction into strain MG1655 ΔaceB Δgcl ΔglcDEFGB::Km.

The kanamycin resistant transformants are then selected and the deletion of the gene ΔaldA::Cm is verified by a PCR analysis with the previously defined oligonucleotides YdcFCf and gapCCR. The strain retained is designated MG1655 ΔaceB Δgcl ΔglcDEFGB::Km ΔaldA::Cm.

The kanamycin and chloramphenicol resistance cassettes can then be eliminated. The plasmid pCP20 carrying FLP recombinase acting at the FRT sites of the kanamycin and the chloramphenicol resistance cassettes is then introduced into the recombinant sites by electroporation. After a series of cultures at 42° C., the loss of the kanamycin and chloramphenicol resistance cassettes is verified by a PCR analysis with the same oligonucleotides as used previously (glcBF/glcDR and YdcFCf/gapCCR). The strain retained is designated MG1655 ΔaceB Δgcl ΔglcDEFGB ΔaldA.

The pME101-ycdW plasmid is then introduced in the strain MG1655 ΔaceB Δgcl ΔglcDEFGB ΔaldA.

Example 4

Construction of Strains with Increased Flux in the Glyoxylate Pathway: MG1655 ΔaceB Δgcl ΔglcDEFGB ΔaldA ΔiclR (pME101-ycdW)

The iclR gene deletion is introduced in the MG1655 ΔaceB Δgcl ΔglcDEFGB ΔaldA using the same strategy as previously described with the following oligonucleotides DiclF
(SEQ ID NO 25)
Cgcacccattcccgcgaaacgcggcagaaaacccgccgttgccaccgcac cagcgactggacaggttcagtctttaacgcgTGTAGGCTGGAGCTGCTTC

G with
 a region (lower case) homologous to the sequence (4221202-4221120) of the gene iclR (reference sequence on the website http://genolist.pasteur.fr/Colibri/),
 a region (upper case) for the amplification of the kanamycin resistance cassette (reference sequence in Datsenko, K. A. & Wanner, B. L., 2000, PNAS, 97: 6640-6645), DiclR
(SEQ ID NO 26)
gcgcattccaccgtacgccagcgtcacttccttcgccgctttaatcacca tcgcgccaaactcggtcacgcggtcatcggCATATGAATATCCTCCTTAG with
 a region (lower case) homologous to the sequence (4220386-4220465) of the gene iclR (reference sequence on the website http://genolist.pasteur.fr/Colibri/),
 a region (upper case) for the amplification of the kanamycin resistance cassette (reference sequence in Datsenko, K. A. & Wanner, B. L., 2000, PNAS, 97: 6640-6645).

The oligonucleotides DiclF and DiclR are used to amplify the kanamycin resistance cassette from the plasmid pKD4. The PCR product obtained is then introduced by electroporation into the strain MG1655 ΔaceB Δgcl ΔglcDEFGB ΔaldA (pKD46). The kanamycin resistant transformants are then selected and the insertion of the resistance cassette is verified by a PCR analysis with the oligonucleotides iclF and iclR defined below. The strain retained is designated MG1655 ΔaceB Δgcl ΔglcDEFGB ΔaldA ΔiclR::Km IclF
(SEQ ID NO 27):
cctttgaggtcgcatggccagtcggc (homologous to the sequence from 4221558 to 4221533).

iclR
(SEQ ID NO 28):
gcttttaatagaggcgtcgccagctccttgcc (homologous to the sequence from 4219917 to 4219949).

The kanamycin resistance cassette can then be eliminated. The plasmid pCP20 carrying FLP recombinase acting at the FRT sites of the kanamycin resistance cassette is then introduced into the recombinant sites by electroporation. After a series of cultures at 42° C., the loss of the kanamycin resistance cassette is verified by a PCR analysis with the same oligonucleotides as used previously (iclF and iclR). The strain retained is designated MG1655 ΔaceB Δgcl ΔglcDEFGB ΔaldA Δicl/R.

The pME101-ycdW plasmid is then introduced in the strain MG1655 ΔaceB Δgcl ΔglcDEFGB ΔaldA ΔiclR.

Example 5

Construction of Strains with Increased NADPH Availability: MG1655 ΔaceB Δgcl ΔiclR ΔglcDEFGB ΔaldA Δedd-eda (pME101-ycdW)

The edd-eda genes are deleted in the MG1655 ΔaceB Δgcl ΔglcB ΔglcDEF ΔaldA ΔiclR strain by transduction. The strain MG1655 Δedd-eda::Cm is first constructed using the same method as previously described with the following oligonucleotides DeddF
(SEQ ID NO 29)
Cgcgcgagactcgctctgcttatctcgcccggatagaacaagcgaaaact tcgaccgttcatcgttcgcagttggcatgcggTGTAGGCTGGAGCTGCTT

CG with
- a region (lower case) homologous to the sequence (1932582-1932500) of the region of the genes edd-eda (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645),

```
DedaR
                                        (SEQ ID NO 30)
gcttagcgccttctacagcttcacgcgccagcttagtaatgcggtcgtaa tcgcccgcttccagcgcatctgccggaaccCATATGAATATCCTCCTTAG
``` with
- a region (lower case) homologous to the sequence (1930144-1930223) of the region of the genes edd-eda (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645),
- The oligonucleotides DeddF and DedaR are used to amplify the chloramphenicol resistance cassette from the plasmid pKD3. The PCR product obtained is then introduced by electroporation into the strain MG1655 (pKD46). The chloramphenicol resistant transformants are then selected and the insertion of the resistance cassette is verified by a PCR analysis with the oligonucleotides eddF and edaR defined below. The strain retained is designated MG1655 Δedd-eda::Cm.

```
eddF
                                        (SEQ ID NO 31):
Gggtagactccattactgaggcgtgggcg (homologous to the sequence from 1932996 to 1932968).

edaR
                                        (SEQ ID NO 32):
ccacatgataccgggatggtgacg (homologous to the sequence from 1929754 to 1929777).
```

To transfer the deletion Δedd-eda::Cm, the method of phage P1 transduction as previously described is used. The preparation of the phage lysate of the strain MG1655 Δedd-eda::Cm was used for the transduction into strain MG1655 ΔaceB Δgcl ΔglcDEFGB ΔaldA ΔiclR.

The chloramphenicol resistant transformants are then selected and the deletion of the gene Δedd-eda::Cm is verified by a PCR analysis with the oligonucleotides eddF and edaR. The strain retained is designated MG1655 ΔaceB Δgcl ΔglcB ΔglcDEF ΔaldA ΔiclR Δedd-eda::Cm.

The chloramphenicol resistance cassette can then be eliminated. The plasmid pCP20 carrying FLP recombinase acting at the FRT sites of the chloramphenicol resistance cassette is then introduced into the recombinant sites by electroporation. After a series of cultures at 42° C., the loss of the chloramphenicol resistance cassette is verified by a PCR analysis with the same oligonucleotides as used previously (eddF and edaR). The strain retained is designated MG1655 ΔaceB Δgcl ΔglcDEFGB ΔaldA ΔiclR Δedd-eda.

The pME101-ycdW plasmid is then introduced in the strain MG1655 ΔaceB Δgcl ΔglcDEFGB ΔaldA ΔiclR Δedd-eda.

Example 6

Construction of Strains with Increased NADPH Availability: MG1655 ΔaceB Δgcl ΔiclR ΔglcDEFGB ΔaldA Δpgi::Cm Δedd-eda (pME101-ycdW)

The pgi gene deletion is introduced in the MG1655 ΔaceB Δgcl ΔglcB ΔglcDEF ΔaldA ΔiclR Δedd-eda using the same strategy as previously described with the following oligonucleotides:

```
DpgiF
                                        (SEQ ID NO 33)
ccaacgcagaccgctgcctggcaggcactacagaaacacttcgatgaaat gaaagacgttacgatcgccgatctttttgcTGTAGGCTGGAGCTGCTTCG
``` with
- a region (lower case) homologous to the sequence (4231352-4231432) of the gene pgi (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645),

```
DpgiR
                                        (SEQ ID NO 34)
gcgccacgctttatagcggttaatcagaccattggtcgagctatcgtggc tgctgatttctttatcatctttcagctctgCATATGAATATCCTCCTTAG
``` with
- a region (lower case) homologous to the sequence (4232980-4232901) of the gene pgi (reference sequence on the website http://genolist.pasteur.fr/Colibri/),
- a region (upper case) for the amplification of the chloramphenicol resistance cassette (reference sequence in Datsenko, K. A. & Wanner, B. L., 2000, PNAS, 97: 6640-6645), The oligonucleotides DpgiF and DpgiR are used to amplify the chloramphenicol resistance cassette from the plasmid pKD3. The PCR product obtained is then introduced by electroporation into the strain MG1655 ΔaceB Δgcl ΔglcB ΔglcDEF ΔaldA ΔiclR Δedd-eda (pKD46). The chloramphenicol resistant transformants are then selected and the insertion of the resistance cassette is verified by a PCR analysis with the oligonucleotides pgiF and pgiR defined below. The strain retained is designated MG1655 ΔaceB Δgcl ΔglcB ΔglcDEF ΔaldA ΔiclR Δedd-eda Δpgi::Cm

```
pgiF
                                        (SEQ ID NO 35):
gcggggcggttgtcaacgatggggtcatgc (homologous to the sequence from 4231138 to 4231167).

pgiR
                                        (SEQ ID NO 36):
cggtatgatttccgttaaattacagacaag (homologous to the sequence from 4233220 to 4233191).
```

The pME101-ycdW plasmid is then introduced in the strain MG1655 ΔaceB Δgcl ΔglcDEFGB ΔaldA ΔiclR Δedd-eda Δpgi::Cm.

Example 7

Construction of Strains with Increased NADPH Availability: MG1655 ΔaceB Δgcl ΔiclR ΔglcDEFGB ΔaldA Δpgi Δedd-eda::Cm ΔudhA::Km (pME101-ycdW)

The udhA gene deletion is introduced in the MG1655 ΔaceB Δgcl ΔglcDEFGB ΔaldA ΔiclR Δpgi::Cm Δedd-eda using the same strategy as previously described with the following oligonucleotides:

DudhAF (SEQ ID NO 37)
CCCAGAATCTCTTTTGTTTCCCGATGGAACAAAATTTTCAGCGTGCCCAC

GTTCATGCCGACGATTTGTGCGCGTGCCAG<u>TGTAGGCTGGAGCTGCTTC</u> with
- a region (boldface letters) homologous to the sequence (4157588-4157667) of the gene udhA (reference sequence on the website http://genolist.pasteur.fr/Colibri/),
- a region (underlined letters) for the amplification of the kanamycin resistance cassette (reference sequence in Datsenko, K. A. & Wanner, B. L., 2000, PNAS, 97: 6640-6645), DudhAR (SEQ ID NO 38)
GGTGCGCGCGTCGCAGTTATCGAGCGTTATCAAAATGTTGGCGGCGGTTG CACCCACTGGGGCACCATCCCGTCGAAAGC<u>CATATGAATATCCTCCTTAG</u> with
- a region (boldface letters) homologous to the sequence (4158729-4158650) of the gene udhA (reference sequence on the website http://genolist.pasteur.fr/Colibri),
- a region (underlined letters) for the amplification of the kanamycin resistance cassette (reference sequence in Datsenko, K. A. & Wanner, B. L., 2000, PNAS, 97: 6640-6645), The oligonucleotides DudhAF and DudhAR are used to amplify the kanamycin resistance cassette from the plasmid pKD4. The PCR product obtained is then introduced by electroporation into the strain MG1655 ΔaceB Δgcl ΔglcDEFGB ΔaldA ΔiclR Δpgi::Cm Δedd-eda (pKD46). The kanamycin resistant transformants are then selected and the insertion of the resistance cassette is verified by a PCR analysis with the oligonucleotides udhAF and udhAR defined below. The strain retained is designated MG1655 ΔaceB Δgcl ΔglcDEFGB ΔaldA ΔiclR Δpgi::Cm Δedd-eda ΔudhA::Km udhAF (SEQ ID NO 39):
(homologous to the sequence from 4157088 to 4157108). GATGCTGGAAGATGGTCACT udhAR (SEQ ID NO 40):
(homologous to the sequence from 4159070 to 4159052). gtgaatgaacggtaacgc The pME101-ycdW plasmid is then introduced in the strain MG1655 ΔaceB Δgcl ΔglcDEFGB ΔaldA ΔiclR Δpgi::Cm Δedd-eda ΔudhA::Km.

Example 8

Fermentation of Glycolic Acid Producing Strains in Erlenmeyer Flasks

Performances of strains were initially assessed in 250 ml baffled Erlenmeyer flask cultures using modified M9 medium (Anderson, 1946, *Proc. Natl. Acad. Sci. USA* 32:120-128) that was supplemented with 40 g/l MOPS and 10 g/l glucose and adjusted at pH 6.8. Spectinomycin was added if necessary at a concentration of 50 mg/l and 100 μm IPTG was also added for induction of the expression vector, if present. An overnight preculture was used to inoculate a 50 ml culture to an $OD_{600\ nm}$ of about 0.3. The cultures were kept on a shaker at 30° C. and 400 rpm until the glucose in the culture medium was exhausted. At the end of the culture, glucose and glycolic acid were analyzed by HPLC using a Biorad HPX 97H column for the separation and a refractometer for the detection.

Comparison of the performances of the different strains is given in table below (each value is the mean of n repetitions). The strain described in example 1 did not show any production of glycolic acid.

| Strain from example n° | 2 | 3 | 4 | 5 | 6 | 7 |
|---|---|---|---|---|---|---|
| Genotype (*E. coli* MG1655) | ΔaceB Δgcl ΔglcB (pME101-ycdW) | ΔaceB Δgcl ΔglcDEFGB ΔaldA (pME101-ycdW) | ΔaceB Δgcl ΔglcDEFGB ΔaldA ΔiclR (pME101-ycdW) | ΔaceB Δgcl ΔglcDEFGB ΔaldA ΔiclR Δedd-eda (pME101-ycdW) | ΔaceB Δgcl ΔglcDEFGB ΔaldA ΔiclR Δedd-eda Δpgi (pME101-ycdW) | ΔaceB Δgcl ΔglcDEFGB ΔaldA ΔiclR Δedd-eda Δpgi ΔudhA (pME101-ycdW) |
| Glycolic acid production (g/l) | 0.28 (n = 3) | 0.28 (n = 8) | 0.65 (n = 8) | 1.73 (n = 8) | 2.75 (n = 6) | 2.33 (n = 4) |
| Yield (g glycolic acid/ g glucose) | 0.03 (n = 3) | 0.03 (n = 8) | 0.07 (n = 8) | 0.17 (n = 8) | 0.29 (n = 6) | 0.25 (n = 4) |

Strains described in example 6 and example 7 are the best producers of glycolic acid with titers higher than 2 g/l and yields higher than 0.2 g/g.

Example 9

Fermentation of Glycolic Acid Producing Strains in Fed Batch Fermentor

The strains described in example 6 and in example 7 were assessed under production conditions in a 600 ml fermentor using a fed batch protocol.

A first preculture in tubes was carried out in LB medium supplemented with 2.5 g/l of glucose at 30° C. followed by a second preculture in 500 ml Erlenmeyer flask filled with 50 ml of synthetic medium supplemented with 40 g/l of MOPS and 10 g/l of glucose (the same medium used for flask cultures) at 30° C. This second preculture was used for inoculation of the fermentor.

The fermentor filled with 200 ml of synthetic medium supplemented with 40 g/l of glucose, 50 mg/l of spectinomycin and 100 μM IPTG was inoculated at an initial optical density of about 2. The culture was carried out at 30° C. with agitation and aeration adjusted to maintain the dissolved oxygen above 30% saturation. The pH was adjusted at 6.8 with base addition. The culture was conducted in a batch mode until exhaustion of glucose. At that time, a solution of 500 g/l glucose supplemented with magnesium sulfate, oligo-elements, spectinomycin and IPTG was added to restore a concentration of 40 g/l of glucose in the medium. Other additions were done each time glucose became exhausted again.

Routinely, strain described in example 7 gave better production performance than strain described in example 6 in fermentors (yield from glucose 0.22 g/g versus 0.15 g/g).

A representative time-course of fermentation for production of glycolic acid using strain of example 7 is given below.

| Time (h) | $OD_{600\,nm}$ (AU) | Glucose (g/l) | Glycolic acid (g/l) |
|---|---|---|---|
| 0 | 2.0 | 35.45 | 0.11 |
| 16 | 3.7 | 34.70 | 0.57 |
| 20 | 5.1 | 33.25 | 1.14 |
| 25 | 6.7 | 31.24 | 1.81 |
| 39 | 14.8 | 20.55 | 4.75 |
| 44 | 20.3 | 12.24 | 7.02 |
| 49 | 27.9 | 2.48 | 9.44 |
| 64 | 53.9 | 7.94 | 18.80 |
| 70 | 62.8 | 33.97 | 21.76 |
| 73 | 67.8 | 24.54 | 23.54 |
| 87 | 84.0 | 36.60 | 28.70 |
| 93 | 89.6 | 25.61 | 31.33 |

The final titre obtained was 31 g/l glycolic acid with a yield on glucose of 0.22 g/g.

---

The invention claimed is:

1. A method for the fermentative production of glycolic acid (glycolate), the method comprising:

culturing a strain of *Escherichia coli* (*E. coli*) in an appropriate culture medium comprising a fermentable source of carbon, the culturing comprising:

a) fermenting the strain of *E. coli* to produce glycolic acid by converting the fermentable source of carbon into glycolic acid, b) concentrating the glycolic acid in the strain of *E. coli* or in the medium, and c) recovering the glycolic acid from the culture medium;

wherein the fermentable source of carbon is glucose; and
wherein the strain of *E. coli* comprises:
  a modification that attenuates the expression of at least one gene selected from the group consisting of:
    aceB encoding malate synthase,
    glcB encoding the second malate synthase, and
    gcl encoding glyoxylate carboligase; and
  a modification that increases the expression of a ycdW or a yiaE gene encoding a polypeptide with NADPH dependent glyoxylate reductase activity that catalyzes the conversion of glyoxylate to glycolate.

2. The method as claimed in claim 1, wherein the ycdW or yiaE gene is endogenous.

3. The method as claimed in claim 1, wherein the modification increases the expression of the ycdW gene.

4. The method as claimed in claim 1, wherein the strain of *E. coli* comprises modifications that attenuate the expression of aceB encoding malate synthase, glcB encoding the second malate synthase, and gcl encoding glyoxylate carboligase.

5. The method as claimed in claim 4, wherein the modification increases the expression of the ycdW gene.

6. The method as claimed in claim 5, wherein the strain of *E. coli* is MG1655.

7. The method as claimed in claim 1, wherein the strain of *E. coli* is further modified by attenuating the expression of at least one gene selected from the group consisting of:
  glcDEF encoding glycolate oxidase, and
  aldA encoding glycoaldehyde dehydrogenase.

8. The method as claimed in claim 1, wherein the strain of *E. coli* is further transformed to increase the glyoxylate pathway flux, by:
  attenuating the activity of the enzyme isocitrate dehydrogenase;
  attenuating the expression of at least one gene selected from the group consisting of:
    pta encoding phospho-transacetylase,
    ack encoding acetate kinase, and
    poxB encoding pyruvate oxidase; or
  increasing the activity of aceA.

9. The method as claimed in claim 8, wherein the activity of aceA is increased by attenuating the expression of the genes iclR or fadR.

10. The method as claimed in claim 1 wherein the availability of NADPH is increased.

11. The method as claimed in claim 10 wherein the strain of *E. coli* further comprises a modification that attenuates the expression of at least one gene selected from the group consisting of:
  pgi encoding the glucose-6-phosphate isomerase,
  udhA encoding the soluble transhydrogenase, and
  edd encoding phosphogluconate dehydratase.

12. The method as claimed in claim 1, wherein glycolate is recovered through a step of depolymerization of glycolate dimers.

13. The method as claimed in claim 1, wherein glycolate is recovered by depolymerization from at least one of glycolate dimers, oligomers and polymers.

14. The method as claimed in claim 1, wherein the strain of *E. coli* comprises modifications that attenuate the expression of aceB encoding malate synthase and gcl encoding glyoxylate carboligase, and the modification that increases the expression of the ycdW or the yiaE gene, and further comprises modifications that attenuate the expression of glcDEF encoding glycolate oxidase, and aldA encoding glycoaldehyde dehydrogenase.

15. The method as claimed in claim 14, wherein the strain of *E. coli* is further transformed to increase the glyoxylate pathway flux, by:
  attenuating the activity of the enzyme isocitrate dehydrogenase;
  attenuating the expression of at least one gene selected from the group consisting of:
    pta encoding phospho-transacetylase,
    ack encoding acetate kinase, and
    poxB encoding pyruvate oxidase; or
  increasing the activity of aceA.

16. The method as claimed in claim 15, wherein the activity of aceA is increased by attenuating the expression of the genes iclR or fadR.

17. The method as claimed in claim 16, wherein the strain of *E. coli* further comprises a modification that attenuates the expression of at least one gene selected from the group consisting of:
  pgi encoding the glucose-6-phosphate isomerase,
  udhA encoding the soluble transhydrogenase, and
  edd encoding phosphogluconate dehydratase.

18. The method as claimed in claim 17, wherein the strain of *E. coli* comprises a modification that increases the expression of the ycdW gene.

19. The method as claimed in claim 18, wherein the strain of *E. coli* is MG1655.

20. The method as claimed in claim 15, wherein the strain of *E. coli* comprises a modification that increases the expression of the ycdW gene.

21. The method as claimed in claim 20, wherein the strain of *E. coli* is MG1655.

22. The method as claimed in claim 15, wherein the strain of *E. coli* further comprises a modification that attenuates the expression of iclR gene.

23. The method as claimed in claim 22, wherein the strain of *E. coli* comprises a modification that increases the expression of the ycdW gene.

24. The method of claim 23, wherein the strain of *E. coli* is MG1655.

25. The method as claimed in claim 22, wherein the strain of *E. coli* further comprises a modification that attenuates the expression of edd and eda genes.

26. The method as claimed in claim 25, wherein the strain of *E. coli* comprises a modification that increases the expression of the ycdW gene.

27. The method as claimed in claim 26, wherein the strain of *E. coli* is MG1655.

28. The method as claimed in claim 25, wherein the strain of *E. coli* further comprises a modification that attenuates the expression of pgi gene encoding the glucose-6-phosphate isomerase.

29. The method as claimed in claim 28, wherein the strain of *E. coli* comprises a modification that increases the expression of the ycdW gene.

30. The method as claimed in claim 28, wherein the strain of *E. coli* is MG1655.

31. The method as claimed in claim 28, wherein the strain of *E. coli* further comprises a modification that attenuates the expression of udhA gene encoding the soluble transhydrogenase.

32. The method as claimed in claim 31, wherein the strain of *E. coli* comprises a modification that increases the expression of the ycdW gene.

33. The method as claimed in claim 32, wherein the strain of *E. coli* is MG1655.

* * * * *